(12) United States Patent
Lewis, II et al.

(10) Patent No.: US 9,585,822 B2
(45) Date of Patent: *Mar. 7, 2017

(54) METHODS OF PREPARING AND USING BOTANICAL ANTIOXIDANT COMPOSITIONS

(71) Applicant: US COSMECEUTECHS, LLC, Richmond, VA (US)

(72) Inventors: Joseph Abernathy Lewis, II, Chesterfield, VA (US); Joseph C. Dinardo, Vesuvius, VA (US)

(73) Assignee: PCR TECHNOLOGY HOLDINGS, LC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/083,314

(22) Filed: Mar. 29, 2016

(65) Prior Publication Data

US 2016/0206536 A1    Jul. 21, 2016

Related U.S. Application Data

(63) Continuation of application No. 14/234,649, filed as application No. PCT/US2012/047790 on Jul. 23, 2012, now Pat. No. 9,326,932.

(60) Provisional application No. 61/511,382, filed on Jul. 25, 2011.

(51) Int. Cl.

| | |
|---|---|
| A61K 8/37 | (2006.01) |
| A61K 8/34 | (2006.01) |
| A61K 8/36 | (2006.01) |
| A61K 8/365 | (2006.01) |
| A61K 8/368 | (2006.01) |
| A61K 8/49 | (2006.01) |
| A61K 8/67 | (2006.01) |
| A61Q 19/06 | (2006.01) |
| A61Q 19/08 | (2006.01) |
| A61K 8/97 | (2006.01) |
| A61Q 19/00 | (2006.01) |
| A61K 8/02 | (2006.01) |
| A61Q 17/00 | (2006.01) |
| A61Q 17/04 | (2006.01) |
| A61Q 19/10 | (2006.01) |

(52) U.S. Cl.
CPC ............ *A61K 8/375* (2013.01); *A61K 8/0216* (2013.01); *A61K 8/347* (2013.01); *A61K 8/36* (2013.01); *A61K 8/365* (2013.01); *A61K 8/368* (2013.01); *A61K 8/498* (2013.01); *A61K 8/4926* (2013.01); *A61K 8/673* (2013.01); *A61K 8/676* (2013.01); *A61K 8/678* (2013.01); *A61K 8/97* (2013.01); *A61Q 17/00* (2013.01); *A61Q 17/04* (2013.01); *A61Q 19/00* (2013.01); *A61Q 19/007* (2013.01); *A61Q 19/06* (2013.01); *A61Q 19/08* (2013.01); *A61Q 19/10* (2013.01); *A61K 2800/28* (2013.01); *A61K 2800/30* (2013.01); *A61K 2800/52* (2013.01); *A61K 2800/522* (2013.01); *A61K 2800/596* (2013.01); *A61K 2800/5922* (2013.01); *A61K 2800/70* (2013.01)

(58) Field of Classification Search
None
See application file for complete search history.

(56) References Cited

U.S. PATENT DOCUMENTS

| | | | |
|---|---|---|---|
| 4,144,325 A | 3/1979 | Voyt | |
| 4,248,861 A | 2/1981 | Schutt | |
| 5,384,123 A | 1/1995 | Metsada | |
| 5,804,168 A | 9/1998 | Murad | |
| 6,207,694 B1 | 3/2001 | Murad | |
| 7,132,296 B2 | 11/2006 | Ou et al. | |
| 7,357,950 B2* | 4/2008 | Mazzio | ........................ 424/404 |
| 7,959,957 B2 | 6/2011 | Miljkovic | |
| 8,048,456 B2* | 11/2011 | Burke-Colvin | ........ A61K 8/585 424/401 |
| 2004/0241286 A1 | 12/2004 | Markwell et al. | |
| 2005/0154054 A1 | 7/2005 | Zielinski et al. | |
| 2006/0002884 A1 | 1/2006 | Golz-Berner et al. | |
| 2008/0124409 A1 | 5/2008 | Zimmerman et al. | |
| 2009/0074822 A1 | 3/2009 | DeClercq et al. | |
| 2009/0220623 A1 | 9/2009 | Mitra et al. | |
| 2010/0272790 A1 | 10/2010 | Morariu | |
| 2014/0179747 A1 | 6/2014 | Lewis, II et al. | |

FOREIGN PATENT DOCUMENTS

| | | |
|---|---|---|
| DE | 10231468 A1 | 2/2004 |
| EP | 2263470 A2 | 12/2010 |

(Continued)

OTHER PUBLICATIONS

Prance, Cocoa re-emerges as beneficial skin care ingredient, May 11, 2007.*
The skin benefits of green tea extract, Mar. 20, 2011.*
Inja Bogdan Allemann, et al., "Botanicals in skin care products", International Journal of Dermatology, 48(9), pp. 923-934, Sep. 2009 (Sep. 2009).
Database GNPD [Online] MINTEL; Jun. 1, 2011, Love Life Skin: "Restorative Moisturizer" XP002742850.
Database GNPD [Online] MINTEL; Oct. 1, 2007, Jurlique: "Wrinkle Softener Beauty Cream", XP002742851.

(Continued)

*Primary Examiner* — Robert A Wax
*Assistant Examiner* — Melissa Mercier
(74) *Attorney, Agent, or Firm* — Leydig, Voit & Mayer, Ltd.

(57) ABSTRACT

A method of improving the appearance of skin, involves topically administering to a subject in need thereof a botanical antioxidant composition having a botanical antioxidant extract blend with: (a) at least one hydroxycinnamic acid, and (b) a *camellia sinesis, vitis vinifera, euterpe oleracea, curcuma longa,* and/or *theobroma cacao* extract, wherein the composition is in cream, lotion, solution, serum, anhydrous preparation, emulsion, microemulsion, multiple emulsion, gel, solid stick, ointment, dry powder, spray, or aerosol form.

24 Claims, No Drawings

(56) References Cited

FOREIGN PATENT DOCUMENTS

| EP | 2736484 A1 | 6/2014 | |
|---|---|---|---|
| FR | 2695318 A1 | 3/1994 | |
| WO | WO 2007026101 A1 | 3/2007 | |
| WO | WO 2008073684 A1 * | 6/2008 | ............. A61K 8/365 |

OTHER PUBLICATIONS

Boxin, et al., "Development and Validation of an Improved Oxygen Radical Absorbance Capacity Assay Using Fluorescein as the Fluorescent Probe", J. Agric. Food Chem., vol. 49, Nr. 10, Oct. 2001, pp. 4619-41926, American Chemical Society.

Huang, et al., "Development and Validation of Oxygen Radical Absorbance Capacity Assay for Lipophilic Antioxidants Using Randomly Methylated β- Cyclodextrin as the Solubility Enhancer", J. Agric. Food Chem., vol. 50, Nr. 7, Mar. 27, 2002, pp. 1815-1821.

Cao, et al., "Oxygen-Radical Absorbance Capacity Assay for Antioxidants", Free Radical Biology & Medicine, vol. 14, Nr. 3, Mar. 1993, pp. 303-311.

Voelckel, "Vorkommen und Photo-Isomerisierung der Urocaninsäure im Stratum corneum bei polymorpher Lichtdermatose (PLD). Vergleichende Untersuchung bei PLD-Patienten und Hautgesunden", Neue Entwicklungen in der Dermatologie, Dec. 1990, pp. 58-72.

Michiels, et al., „Cytotoxicity of linoleic acid peroxide, malondialdehyde and 4-hydroxynonenal towards human fibroblasts, Toxicology an International Journal Concerned with the Effects of Chemicals on Living Systems, vol. 66, Nr. 1, Feb. 11, 1991, pp. 225-234.

Deflandre, et al., "Photostability Assessment of Sunscreens. Benzylidene Camphor and Dibenzoylmethane Derivatives" International Journal of Cosmetic Science 10, Mar. 1988, pp. 53-62.

Thiele, et al., "Depletion of Human Stratum Corneum Vitamin E: An Early and Sensitive In Vivo Marker of UV Induced Photo-Oxidation", The Journal of Investigative Dermatology, vol. 110, Nr. 5, May 1998, 756-761.

Miyachi, et al., "Skin Diseases Associated with Oxidative Injury", Oxidative Stress in Dermatology, Jun. 23, 1993, pp. 323-331.

U.S. Appl. No. 15/083,313, filed Mar. 29, 2016.

U.S. Appl. No. 14/234,649, filed Jan. 24, 2014.

* cited by examiner

METHODS OF PREPARING AND USING BOTANICAL ANTIOXIDANT COMPOSITIONS

CROSS-REFERENCE TO RELATED APPLICATIONS

The present application is a continuing application of U.S. application Ser. No. 14/234,649 filed on Jan. 24, 2014, i.e., the U.S. national stage of international application PCT/US2012/047790, filed on Jul. 23, 2012, claiming the benefit of U.S. Provisional Appl. Ser. No. 61/511,382, filed on Jul. 25, 2011, each of which is incorporated in its entirety herein.

FIELD

The present invention relates to topical cosmetic or dermatological compositions containing an effective amount of a botanical antioxidant extract blend. In particular, the invention relates to compositions comprising the botanical antioxidant extract blend that provide effective protection from damaging oxidation processes in the skin, and also provide protection for the compositions themselves from damaging oxidation processes.

BACKGROUND

Skin is exposed to damage resulting from various sources, including both environmental factors and biochemical processes. Oxidative processes damage proteins, lipids, and other cellular components necessary to maintain the health and appearance of skin, resulting in skin changes, such as skin aging, hyperpigmentation, UV damage, lines, wrinkles, uneven skin texture, etc. Oxidative damage to the skin and its more detailed causes are described in Myachi, Y., "Skin Diseases Associated with Oxidative Injury," In: Fuchs, J., Packer, L. (eds.), "Oxidative Stress in Dermatology." Marcel Dekker, New York, pp. 323-331 (1993).

The damaging effects of the UV part of solar radiation on the skin are generally known. While rays having a wavelength less than 290 nm (the UVC range), are absorbed by the ozone layer in the earth's atmosphere, rays in the range between 290 nm and 320 nm (the UVB range), cause an erythema, simple sunburn or even more or less severe burns. The narrower range around 308 nm is given as a maximum for erythema activity of sunlight. For protection against UVB radiation, numerous compounds are known, including derivatives of 3-benzylidene camphor, 4-aminobenzoic acid, cinnamic acid, salicylic acid, benzophenone, and 2-phenyl-benzimidazole. Also, for the range between about 320 nm and about 400 nm (the UVA range) it is important to have filter substances available, since UVA rays can cause reactions in light-sensitive skin. It has been demonstrated that UVA radiation leads to damage of the elastic and collagenic fibers of the connective tissue, which allows the skin to age prematurely, and that it is to be regarded as a cause of numerous phototoxic and photoallergic reactions. The damaging influence of UVB radiation can be amplified by UVA radiation. It has also been demonstrated that consumption of lipophilic antioxidants, for example, alpha-tocopherol, is triggered in the skin by UVA and UVB radiation. Thiele, J. J., Traber, M. G., Packer, L., "Depletion of human stratum corneum vitamin E: an early and sensitive in vivo marker of UV induced photo-oxidation," *J. Invest. Dermatol.* 110:756-761 (1998).

Further, UV radiation is ionizing radiation. Hence, there is the risk that ionic species are produced upon UV exposure, which are then able to intervene oxidatively in the biochemical processes.

For protection against the rays of the UVA range, certain derivatives of dibenzoylmethane have therefore been used, the photostability of which is not provided to an adequate extent. Deflandre, A., Lang, G. "Photostability assessment of sunscreens. Benzylidene camphor and dibenzoylmethane derivatives," *Int. J. Cosm. Sci.* 10(2):53-62 (1988). UV radiation, however, can also lead to photochemical reactions, wherein then the photochemical reaction products intervene in the skin mechanism.

Predominantly such photochemical reaction products are free radical compounds, for example hydroxyl radicals. Also, undefined free radical photoproducts, which are produced in the skin itself, can trigger uncontrolled side reactions due to their high reactivity. Singlet oxygen, a non-free radical excited state of the oxygen molecule, however, can occur in UV irradiation, short-lived epoxides and many others. Singlet oxygen, for example, is characterized with respect to the normally existing triplet oxygen (free radical base state) by increased reactivity. Nevertheless, excited, reactive (free radical) triplet states of the oxygen molecule also exist. Furthermore, there is the occurrence of lipid peroxidation products, such as hydroperoxides and aldehydes, wherein first in turn free radical chain reactions can be triggered and to which overall cytotoxic properties have been ascribed. Michiels, C., Ramacle, J., "Cytotoxicity of linoleic acid peroxide malondialdehyde and 4-hydroxynonenal towards human fibroblasts," *Toxicology,* 66:225-234 (1990). Lipid peroxidation is an oxidative process that degrades lipids, wherein free radicals steal electrons from the lipids in cell membranes, causing oxidative stress and cell damage.

Light-sensitive skin includes the disorder photodermatoses (photosensitive eruptions). Further designations for the polymorphic light-dermatosis are PLD, PLE, Mallorca Acne and a plurality of further designations, as are given in the literature. Voelckel, A., et al., "Vorkommen und Photo-Isomerisierung der Urocaninsaure im Stratum Corneum bei polymorpher Lichtdermatose (PLD). Vergleichende Untersuchung bei PLD-Patienten und Hautgesunden," *Zentralblatt Haut-Und Geschlechtskrankheiten* (1989), Springer-Verlag, vol. 156, 1989, pp. 1-15. Erythematous skin symptoms also occur as concomitant symptoms in certain skin diseases or skin irregularities. For example, the typical rash in the clinical picture of acne is regularly reddened to a greater or lesser extent.

It is known that undesirable oxidation processes can occur in the human and animal skin. Such processes play a considerable part in skin aging. In order to prevent these reactions, antioxidants and/or free radical absorbers/scavengers can be incorporated in cosmetic or dermatological formulations to treat or prevent damage caused by oxidative and/or degenerative biochemical processes. Antioxidants are substances that scavenge free radicals and prevent oxidation processes or prevent the auto-oxidation of fats containing unsaturated compounds. Antioxidants used in the field of cosmetics and pharmacy include, for example, alpha-tocopherol, in particular in the form of alpha-tocopheryl acetate, sesamol, colic acid derivatives, butylhydroxy anisole, butylhydroxy toluene, vitamin C, plant-derived polyphenols and flavonoids, and idebenone. For example, it has been proposed to use vitamin E (U.S. Pat. Nos. 4,144,325 and 4,248,861), a substance having known antioxidative action in sunscreen formulations, but even here the action achieved remains far below that hoped for. Tocopherol (a vitamin E antioxidant), for example, degrades to form pro-oxidative products.

While antioxidants and/or free radical absorbers/scavengers have been included in cosmetic and/or dermatological compositions, none of these compositions provide complete protection against undesirable oxidation processes because none contain the proper blend of botanical antioxidant extracts necessary to provide a broad spectrum of antioxidant protection that can significantly (e.g., synergistically) increase the capacity for oxidative stress protection.

SUMMARY

An aspect of the invention provides a method of improving the appearance of skin, comprising topically administering to a subject in need thereof a botanical antioxidant composition comprising a botanical antioxidant extract blend comprising: (a) a hydroxycinnamic acid, and (b) a *camellia sinesis, vitis vinifera, euterpe oleracea, curcuma longa*, and/or *theobroma cacao* extract, wherein the composition is in cream, lotion, solution, serum, anhydrous preparation, emulsion, microemulsion, multiple emulsion, gel, solid stick, ointment, dry powder, spray, or aerosol form.

DETAILED DESCRIPTION

Applicants have now discovered that topical compositions comprising a diverse blend of botanical antioxidant extracts are effective in combating a broad array of undesirable oxidative processes that contribute to skin aging and/or cause skin damage. Thus, the present invention is directed to topical cosmetic and/or dermatological (e.g., anti-aging) compositions containing a botanical antioxidant extract blend, and their use to treat and/or prevent damage to skin caused by oxidative and degenerative processes. Such compositions are believed to provide broad protection from undesirable oxidative processes that affect skin and the convenience of a single composition.

In one embodiment, the invention is a cosmetic or dermatological composition comprising a diverse botanical antioxidant extract blend comprising at least a first antioxidant botanical extract derived from fruit and a second antioxidant botanical extract derived from spice. Desirably, the blend of fruit and spice extract comprises at least one hydroxycinnamic acid and one or more (preferably two or more or three or more) antioxidants selected from the group consisting of vitamins, stilbenoids, curcumininoids, tannins, flavones, flavonols, flavan-3-ols, flavanones, anthocyanidins, anthocyanins, isoflavones, flavanonols, proanthocyanidins, and pyridine alkaloids. In some preferred embodiments the cosmetic or dermatological composition comprises an antioxidant botanical fruit extract selected from the group consisting of seed or fruit extracts from grape, acai fruit, kiwi, raspberry, plum, pomegranate, bearberry, elderberry, grapefruit, black currant, blackberry, cranberry, bilberry, olive, *Lycium Chinese*, cocoa, palm fruit, and combinations thereof, and a antioxidant botanical spice extract selected from the group consisting of turmeric, nutmeg, thyme, sage, poppy seed, rosemary, sage, oregano, black pepper, green peppercorn, white pepper, chili, caraway, dill, parsley, ginger, green cardamom, clove, cinnamon, coriander, Chinese prickly ash, lemon grass, star anise, mint, sweet basil, bay leaf, and combinations thereof, more preferably in further combination with a third antioxidant botanical extract such as *eucommia ulmoides* extract.

In another embodiment, the invention is a cosmetic or dermatological composition comprising a diverse botanical antioxidant extract blend comprising at least a first antioxidant botanical extract comprising at least one hydroxycinnamic acid and a second antioxidant botanical extract comprising at least two additional antioxidants selected from the group consisting of vitamins, stilbenoids, curcumininoids, tannins, flavones, flavonols, flavan-3-ols, flavanones, anthocyanidins, anthocyanins, isoflavones, flavanonols, proanthocyanidins, dihydroxybenzoic acids, and pyridine alkaloids.

In a preferred embodiment, the invention is a cosmetic or dermatological composition comprising a diverse botanical antioxidant extract blend comprising a first antioxidant botanical extract (e.g., a fruit extract or spice extract) comprising at least one hydroxycinnamic acid, a second antioxidant botanical extract (e.g., a fruit extract or spice extract) comprising at least two additional antioxidants selected from the group consisting of vitamins, stilbenoids, curcumininoids, tannins, flavones, flavonols, flavan-3-ols, flavanones, anthocyanidins, anthocyanins, isoflavones, flavanonols, proanthocyanidins, dihydroxybenzoic acids, and pyridine alkaloids, and a third antioxidant botanical extract comprising at least two additional antioxidants selected from the group consisting of vitamins, stilbenoids, curcumininoids, tannins, flavones, flavonols, flavan-3-ols, flavanones, anthocyanidins, anthocyanins, isoflavones, flavanonols, proanthocyanidins, dihydroxybenzoic acids, and pyridine alkaloids.

In another embodiment, the invention is a cosmetic or dermatological composition comprising a diverse botanical antioxidant extract blend comprising a first antioxidant botanical extract (e.g., a fruit extract or spice extract) comprising at least one hydroxycinnamic acid, and a second antioxidant botanical extract (e.g., a fruit extract or spice extract) comprising at least two additional antioxidants selected from the group consisting of vitamins, stilbenoids, curcumininoids, tannins, flavones, flavonols, flavan-3-ols, flavanones, anthocyanidins, anthocyanins, isoflavones, flavanonols, proanthocyanidins, dihydroxybenzoic acids, and pyridine alkaloids, wherein the botanical antioxidant extract blend comprises three or more extracts selected from *eucommia ulmoides, camellia sinesis, vitis vinifera* seed, *euterpe oleracea, curcuma longa*, and *theobroma cacao*.

The botanical antioxidant extract blend of the invention can be used to treat or prevent a wide variety of skin changes, including skin changes resulting from intrinsic aging (i.e., qualitative and quantitative skin changes that result from declining physiologic functions and capabilities such as diminished or defective synthesis of collagen and elastin in the dermis, increased dryness, flattened papillary dermis, and decreased stratum corneum turnover) and extrinsic aging (i.e., qualitative and quantitative skin changes that result from external factors such as ultra-violet radiation (photoaging), cigarette smoking, and air pollution among others). For example, the botanical antioxidant extract blend of the invention can be used to treat or reduce visible signs of intrinsic and/or extrinsic aging such as skin wrinkling and/or fine lines, skin sagging, skin dryness, skin thinness and/or transparency, skin firmness, skin smoothness, nail plate thinning and/or ridging, and the like. In addition, the botanical antioxidant extract blend of the invention can be used to treat or prevent erythematous; inflammatory, allergic or autoimmune-reactive symptoms, in particular dermatoses; skin changes in light-sensitive skin, particularly photodermatoses; and damaging effects of the UV part of solar radiation on the skin such as skin blotchiness and/or darkening, age spots, spider veins, actinic keratoses, and the like.

Thus the invention is also directed to a method of treating or preventing the worsening of a skin change or (e.g., skin aging (e.g., wrinkling, fine lines), hyperpigmentation (e.g., age spots), UV damage, erythematous, cellulitis, rosacea, eczema, dermatitis (atopic or contact), pruritis, and other inflammatory symptoms and skin conditions, photodamage, photoreactions, etc.) comprising topically administering a composition comprising the botanical antioxidant extract blend. Compositions containing the botanical antioxidant extract blend of the present invention can be used to reduce, if not completely prevent, damage to the skin caused by oxidative influence.

In addition, the botanical antioxidant extract blend of the invention can be used to promote skin changes that improve the appearance of skin, including skin tightening, skin brightening, skin illuminating, skin smoothing, skin moistening, skin plumping, skin firming, evening of skin tone, reducing skin redness, minimizing the appearance of dark circles, improving skin elasticity and recoilability, improving overall skin cell health, reducing pore size, and reducing the appearance of fine lines, wrinkles and skin blemishes resulting from acne or aging.

The present invention pertains to diverse botanical antioxidant extract blends, and cosmetic and/or dermatological compositions containing such blends, that promote skin changes that improve skin health or appearance, e.g., by providing the dermal cells a friendly environment in which to undergo natural skin repair processes. In addition, or alternatively, the present invention pertains to a botanical antioxidant blends, and cosmetic and/or dermatological compositions containing such blends, that reduce skin changes that result in unhealthy or unattractive skin, e.g., by preventing damage to lipids, DNA, and proteins, or by protecting the skin against photo-reactions and/or inflammatory reactions.

It is believed that the botanical antioxidant extract blends of the invention provide a synergistic improvement in the capacity for antioxidant and oxidative stress protection. In addition, it is believed that the botanical antioxidant extract blends of the invention provide for an improved skin and/or hair care regimen by providing broad spectrum antioxidative protection in a single composition, preferably without the presence of synthetic antioxidants.

In particular, the invention is a cosmetic or dermatological composition comprising at least two or more (preferably three or more, four or more, five or more, or six or more) different botanical antioxidant extracts wherein the first and second botanical antioxidant extracts contribute different spectrums of antioxidants to the composition. The botanical antioxidant extract blend of the invention can comprise any suitable combination of fruit, spice, vegetable, root, leaf, floral or other botanical antioxidant extracts (e.g., plant extracts).

The diversified botanical antioxidant blend of the invention provide compositions having exceptionally high oxygen radical absorbance capacity (ORAC) values. Indeed, the ORAC values of botanical antioxidant blends of the invention are unexpectedly greater than the weight averaged ORAC value of the constituent extracts, suggesting a "boosting" or synergistic effect of the botanical antioxidant extract blend on free radical scavenging capacity. Oxygen radical absorbance capacity (ORAC) is a method of measuring antioxidant capacities in biological samples in vitro and is described in the following publications. See Cao G, Alessio H, Cutler R. "Oxygen-radical absorbance capacity assay for antioxidants," *Free Radic. Biol. Med.* 14 (3):303-11 (1993); Ou B, Hampsch-Woodill M, Prior R (2001), "Development and validation of an improved oxygen radical absorbance capacity assay using fluorescein as the fluorescent probe," *J. Agric. Food Chem.* 49 (10):4619-26 (2001); Huang, D., et al., *J. Agric. and Food Chem.* 50(7):1815-21 (2002); Ou, B., et al., "Method for Assaying the Antioxidant Capacity of a Sample," U.S. Pat. No. 7,132,296. Desirably the botanical antioxidant blend of the invention provides greater than about 500 units per gram (e.g., greater than about 800 units per gram, greater than about 1000 units per gram, greater than 1500 units per gram, greater than 2000 units per gram, or greater than 2500 units per gram) based on the total dry weight of the botanical antioxidant blend.

Cosmetic and/or dermatological compositions of the invention typically contain about 0.001% to about 20%, based on the total weight of the composition, of a botanical antioxidant extract blend of the invention. Preferably the amount of botanical antioxidant extract blend of the invention included in the cosmetic and/or dermatological compositions of the invention is about 0.01% to about 10%, or about 0.05% to about 5%, or about 0.1% to about 2% (e.g., 1.0 wt. %).

Botanical fruit antioxidant extracts suitable for inclusion in the botanical antioxidant extract blend of the invention include, for example, seed or fruit extracts from grape (*vitis vinifera*), acai fruit (*euterpe oleracea*), kiwi (*Actinidia chinensis*), raspberry (*Rubus idaeus*), pomegranate (*Punica Granatum*), elderberry, grapefruit, plum, black currant, bearberry, blackberry, cranberry (*Vaccinium macrocarpon*), bilberry (*vaccinium myrtillus*), olive (*Olea Europaea*), *Lycium Chinense* (Goji Berry), cocoa (*theobroma cacao*), palm (*Elaeis guineensis*) fruit, and the like.

Botanical spice antioxidant extracts suitable for inclusion in the botanical antioxidant extract blend of the invention include, for example, extracts of turmeric (*curcuma longa*), nutmeg, thyme, sage, poppy seed, rosemary, sage, oregano, black pepper, green peppercorn, white pepper, chili, caraway, dill, parsley, ginger, green cardamom, clove, cinnamon (*Cinnamomum cassia* Presl), coriander, Chinese prickly ash, lemon grass, star anise, mint, sweet basil, bay leaf (*Laurus nobilis* L), and the like. A preferred botanical spice antioxidant extract is turmeric (*curcuma longa*) extract.

Other botanical antioxidant extracts suitable for inclusion in the botanical antioxidant extract blend of the invention include, for example, tea extracts such as green tea (*camellia sinesis*), white tea, black tea, and rooibos extracts, root extracts such as *Scutellaria Baicalensis* root, *Pueraria Lobata* root, Burdock (*arctium lappa*) root, *Panax ginseng* root, and other plant extracts including extracts of alfalfa (*medicago sativa*), edelweiss, eucommia (*eucommia ulmoides*), milk thistle, soy, jiaogulan (*gynostemma pentaphyllum*)(rich in saponins, e.g., gypenosides), *Chamomilla Recutita, Ampelopsis Grossedentata, Gingko Biloba, Madagascar ambiatry* (*Vernonia appendiculata*), carrot, myrtle, hibiscus, sweet pea, and pine bark (*pinus pinaster*).

In one embodiment, the invention is a cosmetic or dermatological composition comprising a diverse botanical antioxidant extract blend comprising at least a first antioxidant botanical extract derived from fruit and a second antioxidant botanical extract derived from spice. Optionally, the cosmetic or dermatological composition of this embodiment comprises three or more (e.g., four or more, or five or more, or six or more) antioxidant botanical extracts, wherein the first antioxidant botanical extract is derived from fruit and the second antioxidant botanical extract is derived from spice, and the additional antioxidant botanical extracts are selected from those described herein. In some preferred embodiments, the first antioxidant botanical extract is selected from grape seed extract, acai fruit extract, blackberry extract, olive leaf extract, and cacao extract, the second antioxidant botanical extract is selected from turmeric extract, nutmeg extract, and oregano extract, and optionally the third antioxidant botanical extract is selected from green tea (*camellia sinesis*), eucommia (*eucommia ulmoides*), and Burdock (*arctium lappa*) root.

When the cosmetic or dermatological composition comprising a diverse botanical antioxidant extract blend comprising at least a first antioxidant botanical extract derived from fruit and a second antioxidant botanical extract derived from spice, the blend of fruit and spice extract desirably comprises at least one hydroxycinnamic acid and one or more (preferably two or more or three or more) antioxidants selected from the group consisting of vitamins, stilbenoids, curcumininoids, tannins, flavones, flavonols, flavan-3-ols, flavanones, anthocyanidins, anthocyanins, isoflavones, flavanonols, proanthocyanidins, dihydroxybenzoic acids, and pyridine alkaloids. In especially preferred embodiments, the cosmetic or dermatological composition comprises three or fewer (e.g., one, two or three) antioxidant botanical extracts derived from fruit and three or fewer (e.g., one, two or three) antioxidant botanical extracts derived from spice.

In another embodiment, the invention is a cosmetic and/or dermatological compositions comprising a botanical antioxidant extract blend comprising (a) a first antioxidant botanical extract (e.g., a fruit extract or a spice extract) comprising at least one hydroxycinnamic acid, and (b) a second antioxidant botanical extract (e.g., a fruit extract or a spice extract) comprising at least one antioxidant selected from the group consisting of vitamins, stilbenoids, curcumininoids, tannins, flavones, flavonols, flavan-3-ols, flavanones, anthocyanidins, anthocyanins, isoflavones, flavanonols, proanthocyanidins, and pyridine alkaloids. Optionally, the cosmetic or dermatological composition of this embodiment comprises three or more (e.g., four or more, or five or more, or six or more) antioxidant botanical extracts, wherein each of the antioxidant botanical extracts are selected from those described herein.

The botanical antioxidant extract blends of the invention can comprise about 50% or more (e.g., about 60% or more, or about 70% or more, or even about 80% or more) of a hydroxycinnamic acid compound, based on the weight of the botanical antioxidant extract blend. For example, the first botanical antioxidant extract preferably comprises about 50% or more (e.g., about 60% or more, or about 70% or more, or even about 80% or more) of a hydroxycinnamic acid compound, based on the weight of the first botanical antioxidant extract.

Typically the hydroxycinnamic acid is selected from the group consisting of alpha-cyano-4-hydroxycinnamic acid, caffeic acid, cichoric acid, cinnamic acid, chlorogenic acid, caftaric acid, coumarin, coumaric acid, coutaric acid, diferulic acid, fertaric acid, ferulic acid, and sinapinic acid. In particularly preferred embodiments, botanical antioxidant blend comprises about 50% or more of a blend of chlorogenic acid and coumaric acid. The hydroxycinnamic acid compound desirably is derived from a food or plant extract, for example, *Echinacea*, strawberries, pineapple, carrots, flaxseeds, potato, coffee, sunflower, blueberries, grape and wine, citrus fruits (e.g., orange), maize, oats, rice, artichoke, apple, peanut, burdock, hawthorn, pear, basil, thyme, oregano, bamboo, *eucommia ulmoides* (i.e., Chinese rubber tree), and the like. Preferably the hydroxycinnamic acid compound is derived from *eucommia ulmoides* extract.

The botanical antioxidant extract blends of the invention desirably comprise at least one additional botanical antioxidant extract comprising at least one antioxidant selected from the group consisting of vitamins, stilbenoids, curcumininoids, tannins, flavones, flavonols, flavan-3-ols, flavanones, anthocyanidins, anthocyanins, isoflavones, flavanonols, proanthocyanidins, dihydroxybenzoic acids, and pyridine alkaloids. In some embodiments, the botanical antioxidant extract blend comprises at least two or more (e.g., a second botanical antioxidant extract, and a third botanical antioxidant extract) botanical antioxidant extracts comprising at least one antioxidant selected from the group consisting of vitamins, stilbenoids, curcumininoids, tannins, flavones, flavonols, flavan-3-ols, flavanones, anthocyanidins, anthocyanins, isoflavones, flavanonols, proanthocyanidins, dihydroxybenzoic acids, and pyridine alkaloids. In other embodiments, the botanical antioxidant extract blend comprises at least three or more (or at least four or more, or at least five or more, or at least six or more) botanical antioxidant extracts comprising at least one antioxidant selected from the group consisting of vitamins, stilbenoids, curcumininoids, tannins, flavones, flavonols, flavan-3-ols, flavanones, anthocyanidins, anthocyanins, isoflavones, flavanonols, proanthocyanidins, dihydroxybenzoic acids, and pyridine alkaloids.

In some embodiments, the botanical antioxidant extract blends of the invention further comprise an extract comprising one or more antioxidant vitamins, which are desirably selected from the group consisting of vitamin B, vitamin C, and vitamin E. The antioxidant vitamin desirably is derived from a food or plant source, for example, green tea, acai, and the like. Preferably the antioxidant vitamin is present in a second or third, etc. botanical antioxidant extracts.

In some embodiments, the botanical antioxidant extract blends of the invention further comprise an extract containing one or more stilbenoids, which are desirably selected from the group consisting of resveratrol, piceatannol, pterostilbene, and astringin. Preferably the stilbenoid is resveratrol and is derived from a food or plant source such as grape seed extract.

In some embodiments, the botanical antioxidant blends of the invention further comprise an extract comprising one or more curcumininoids, which are desirably selected from the group consisting of curcumin, demethoxycurcumin, and bisdemethoxycurcumin. Typically the curcumininoids are derived from turmeric (*curcuma longa*).

In some embodiments, the botanical antioxidant extract blends of the invention further comprise an extract comprising one or more tannins selected from the group consisting of hydrolyzable tannins, gallic acid, gallic acid $C_{1-12}$ alkyl esters, ethyl gallate, propyl gallate, octyl gallate, dodecyl gallate, theaflavin esters of gallic acid, and condensed tannins (e.g., proanthocyanidins, prodelphinidins, procyanidins, oligomeric proanthocyanidins, leukocyanidins, leucoanthocyanins). Preferably the tannin is selected from gallic acid, proanthocyanidins and combinations thereof.

In some embodiments, the botanical antioxidant extract blends of the invention further comprise an extract comprising one or more flavones selected from the group consisting of apigenin, luteolin, tangeritin, chrysin, 6-hydroxyflavone, baicalein, scutellarein, wogonin, and orientin. Preferably the flavone is orientin.

In some embodiments, the botanical antioxidant extract blends of the invention further comprise an extract comprising one or more flavonols selected from the group consisting of 3-hydroxyflavone, azaleatin, fisetin, galangin, gossypetin, isorhamnetin, kaempferide, kaempferol, morin, myricetin, natsudaidain, pachypodol, quercetin, rhamnazin, and rhamnetin. Preferably the flavonol is selected from the group consisting of kaempferol, quercetin, and myricetin and combinations thereof.

In some embodiments, the botanical antioxidant extract blends of the invention further comprise an extract comprising one or more flavan-3-ols selected from the group consisting of catechin, epicatechin, gallocatechin, epigallocatechin, catechin gallate, epicatechin gallate, epigallocatechin gallate, epiafzelechin, fisetinidol, guibourtinidol, mesquitol, robinetinidol. Preferably the flavan-3-ol is selected from the group consisting of catechin, epicatechin, epigallocatechin, epicatechin gallate, epigallocatechin gallate, and combinations thereof.

In some embodiments, the botanical antioxidant extract blends of the invention further comprise an extract comprising one or more flavanones selected from the group consisting of butin, eriodictyol, hesperetin, hesperidin, homoeriodictyol, isosakuranetin, naringenin, pinocembrin, poncirin, sakuranetin, sakuranin, and sterubin.

In some embodiments, the botanical antioxidant extract blends of the invention further comprise an extract comprising one or more anthocyanins selected from the group consisting of aurantinidin, cyaniding, delphinidin, europinidin, luteolinidin, pelargonidin, malvidin, peonidin, petunidin, rosinidin. In some embodiments, the botanical antioxidant extract blends of the invention further comprise an extract comprising one or more isoflavones selected from the group consisting of biochanin, coumestrol, daidzein, formononetin, and genistein. In some embodiments, the botanical antioxidant extract blends of the invention further comprise an extract comprising one or more flavanonols selected from the group consisting of taxifolin and aromadedrin. Preferably the flavanonol is taxifolin.

In some embodiments, the botanical antioxidant extract blends of the invention further comprise an extract comprising one or more pyridine alkaloids selected from the group consisting of trigonelline, arecoline, ricinine, actinidine, gentianine, and gentialutine. Preferably the pyridine alkaloid is trigonelline.

In some embodiments, the botanical antioxidant extract blends of the invention further comprise an extract comprising one or more antioxidant dihydroxybenzoic acid compounds, such as protocatechuic acid.

In other preferred embodiments, the antioxidant blends of the invention further comprise two or more flavanoid antioxidants selected from the group consisting of flavones, flavonols, flavan-3-ols, flavanones, anthocyanidins, anthocyanins, isoflavones, and flavanonols.

In other preferred embodiments, the antioxidant blends of the invention further comprise at least one curcumininoid, at least one proanthocyanidin, at least one flavan-3-ol.

In some preferred embodiments, the antioxidant blend comprises two or more (e.g., three or more, four or more, five or more or six or more) extracts selected from alfalfa (*medicago sativa*), green tea (*camellia sinesis*), turmeric (*curcuma longa*), edelweiss, eucommia (*eucommia ulmoides*), white tea, black tea, grape (*vitis vinifera*) seed, acai fruit (*euterpe oleracea*), cocoa (*theobroma cacao*), milk thistle, soy, thyme, jiaogulan (*gynostemma pentaphyllum*) (rich in saponins, e.g., gypenosides), rooibos, *Chamomilla Recutita, Scutellaria Baicalensis* Root, carrot, kiwi (*Actinidia chinensis*), *Ampelopsis Grossedentata*, raspberry seed (*Rubus idaeus*), pomegranate seed, elderberry seed, grapefruit seed, black currant seed, cranberry seed (*Vaccinium macrocarpon*), bilberry (*vaccinium myrtillus*) seed, *Pueraria Lobata* Root, *Gingko Biloba, Madagascar ambiatry* (*Vernonia appendiculata*), Burdock (*arctium lappa*) root, sage, myrtle, hibiscus, *Panax ginseng* root, olive (*Olea Europaea*) leaf, sweet pea, rosemary, sage, oregano, thyme, black pepper, clove, cinnamon (*Cinnamomum cassia* Presl), coriander, Chinese prickly ash, lemon grass, star anise, mint, sweet basil, bay leaf (*Laurus nobilis* L), and pine bark (*pinus pinaster*) extracts, more preferably eucommia (*eucommia ulmoides*), green tea (*camellia sinesis*), grape (*vitis vinifera*) seed, acai fruit (*euterpe oleracea*), turmeric (*curcuma longa*), and cocoa (*theobroma cacao*) extracts. For example, in some especially preferred embodiments, the antioxidant blend comprises at least eucommia (*eucommia ulmoides*), green tea (*camellia sinesis*), and grape (*vitis vinifera*) seed extracts, optionally in further combination with acai fruit (*euterpe oleracea*), turmeric (*curcuma longa*), and cocoa (*theobroma cacao*) extracts.

In particularly preferred embodiments, the botanical antioxidant extract blend comprises eucommia (*eucommia ulmoides*), green tea (*camellia sinesis*), grape (*vitis vinifera*) seed, acai fruit (*euterpe oleracea*), turmeric (*curcuma longa*), and cocoa (*theobroma cacao*) extracts. More preferably the botanical antioxidant extract blend comprises about 60 wt. % or more (e.g., about 70 wt. % to about 90 wt. %, or about 75 to about 85 wt. %) *eucommia ulmoides* extract, about 5 wt. % to about 25 wt. % (e.g., about 8 to about 20 wt. %, or about 10 to about 17 wt. %) *camellia sinesis* extract, about 10 wt. % or less (e.g., about 0.1 to about 7.0 wt. %, or about 1.0 to about 5.0 wt. %) *vitis vinifera* seed extract, about 5 wt. % or less (e.g., about 0.1 to about 3.0 wt. %, or about 0.5 to about 2.0 wt. %) *euterpe oleracea* extract, about 5 wt. % or less (e.g., about 0.01 to about 1.0 wt. %, or about 0.1 to about 0.7 wt. %) *curcuma longa* extract, and about 5 wt. % or less (e.g., about 0.01 to about 1.0 wt. %, or about 0.1 to about 0.7 wt. %) *theobroma cacao* extract.

The compositions of the present invention typically contain at least one additive. Suitable additives include, but are not limited to, surfactants, cosmetic auxiliaries, pigments, UVA filters, UVB filters, skin absorption promoting agents, propellants, thickening agents, emulsifiers, solvents (e.g., alcoholic solvents), water, perfumes, dyestuffs, deodorants, antimicrobial materials, back-fatting agents, complexing and sequestering agents, exfoliating agents, pearlescent agents, plant extracts, vitamins, active ingredients, and/or derivatives and combinations thereof.

The compositions of the invention optionally further comprise substances which absorb UV radiation in the UVB range, wherein the total quantity of filter substances is, for example 0.1 wt % to 30 wt %, preferably 0.5 to 10 wt %, more preferably 1.0 to 6.0 wt %, based on the total weight of the compositions, in order to provide cosmetic compositions which protect the skin from the entire range of ultraviolet radiation and serve as sunscreen agents for the skin. Suitable UVB filter substances include oil-soluble and water-soluble substances. Advantageous oil-soluble UVB filters include, for example, mineral oils, mineral waxes, oils such as triglycerides of capric or caprylic acid, natural oils such as castor oil, fats, waxes and other natural and synthetic adipoids, preferably esters of fatty acids with alcohols of low C number, for example with isopropanol, propylene glycol or glycerine, or esters of fatty alcohols with alkane acids of low C number or with fatty acids; alkyl benzoates; silicone oils, such as dimethylpolysiloxanes, diethylpolysiloxanes, diphenylpolysiloxanes and mixtures thereof 3-Benzylidene camphor derivatives, preferably 3-(4-methylbenzylidene)

camphor, 3-benzylidene camphor; 4-aminobenzoic acid derivatives, preferably (2-ethylhexyl) 4-(dimethylamino) benzoate, amyl 4-(dimethylamino) benzoate; esters of cinnamic acid, preferably (2-ethylhexyl) 4-methoxycinnamate, isopentyl 4-methoxycinnamate; esters of salicylic acid, preferably (2-ethylhexyl) salicylate, (4-isopropyl-benzyl) salicylate, homomentyl salicylate, derivatives of benzophenone, preferably 2-hydroxy-4-methoxybenzophenone, 2-hydroxy-4-methoxy-4'-methylbenzophenone, 2,2'-dihydroxy-4-methoxybenzophenone; esters of benzylidenemalonic acid, preferably di(2-ethylhexyl) 4-methoxybenzylidenemalonate, 2,4,6-trianilino(p-carbo-2'-ethyl-1'-hexyloxy)-1,3,5-triazine.

Advantageous water-soluble UVB filters include salts of 2-phenylbenzimidazole-5-sulphonic acid (e.g., sodium, potassium or triethanolammonium salts), sulphonic acid and sulphonic acid derivatives of benzophenones, preferably 2-hydroxy-4-methoxy benzophenone-5-sulphonic acid and their salts; sulphonic acid derivatives of 3-benzylidene camphor, such as for example 4-(2-oxo-3-bornylidenemethyl) benzene sulphonic acid, 2-methyl-5-(2-oxo-3-bornylidene-methyl)sulphonic acid and their salts, as well as 1,4-di(2-oxo-10-sulpho-3-bornylidene-methyl)benzene and its salts (the corresponding 10-sulphato compounds, for example the corresponding sodium, potassium or triethanolammonium salt), also designated as benzene-1,4-di(2-oxo-1-bornylidene-methyl)-10-sulphonic acid.

The compositions of the invention also optionally further comprise substances which absorb UV radiation in the UVA range, wherein the total quantity of filter substances is, for example 0.1 wt % to 30 wt %, preferably 0.5 to 10 wt %, more preferably 1.0 to 6.0 wt %, based on the total weight of the compositions, in order to provide cosmetic compositions which protect the skin from the entire range of ultraviolet radiation and serve as sunscreen agents for the skin. Suitable UVA filter substances include derivatives of dibenzoylmethane, in particular 1-(4'-tertbutylphenyl)-3-(4'-methoxyphenyl)propane-1,3-dione and 1-phenyl-3-(4'-isopropyl-phenyl)propane-1,3-dione.

The compositions of the invention can also optionally contain inorganic pigments, which are used conventionally in cosmetics to protect the skin from UV rays. Suitable inorganic pigments include oxides of titanium, zinc, zirconium, silicon, iron, manganese, cerium and mixtures thereof, and modifications in which the oxides are the active agents. Preferably the inorganic pigments are based on titanium dioxide.

In some embodiments, the compositions of the invention comprise both a UVB filter substance and a UVA filter substance. In other embodiments, the compositions comprise a UVB filter and an inorganic pigment or a UVA filter substance and an inorganic pigment. In yet other embodiments, the compositions of the invention comprise a UVB filter substance, a UVA filter substance, and an inorganic pigment.

In other preferred embodiments, the composition further comprises a skin absorption promoting agent. The absorption promoting agents are substances capable of improving the diffusion of active ingredients in the epidermis, in particular the stratum corneum. These adjuvants can be classified in different families according to their chemical structure. Suitable skin absorption promoting agents are known in the art. As an example of absorption promoting agents, dioxolane derivatives such as isopropylidene glycerol, marketed under the name Solketal or 2n-nonyl 1-3 dioxolane; or diethylene glycol monoethyl ether (for example that marketed under the Tradename Transcutol®) can in particular be mentioned. Absorption promoting agents are also described in the following chemical families: polyols, fatty acids, esters of fatty acids alcohols and amides. As an example of substances representative of these families, propylene glycol monocaprylate or Capryol 90, caprylic acid, diisopropyl adipate, polysorbate 80, 2-octyl dodecanol and 1-dodecylazacyclohepta-2-one or Azone, can in particular be mentioned. Substances presenting properties of absorption promoting agents can also be found in the family of sulphoxides (such as for example dimethylsulphoxide), terpenes (for example d-limonene), alkanes (for example N-heptane) or organic acids (for example alpha hydroxy acids such as glycolic acid and lactic acid, and salts thereof, or salicylic acid and salicylates). The quantity of absorption promoting agent in the compositions according to the invention, varies from 2 to 12% by weight of the total composition.

The cosmetic and dermatological compositions of the invention optionally further comprise one or more cosmetic auxiliaries, as are used conventionally in such compositions, for example preservatives, bactericides, perfumes, substances for preventing foaming, dyestuffs, pigments which have a coloring effect, thickening agents, surfactant substances, emulsifiers, softening, moisturizing and/or moisture-retaining substances, exfoliating agents, fats, oils, waxes or other conventional constituents of a cosmetic or dermatological formulation, such as alcohols, polyols, polymers, foam stabilizers, electrolytes, organic solvents or silicone derivatives.

The cosmetic or dermatological compositions of the invention can be conventionally prepared and then used to provide treatment, care, and cleansing of the skin, and as a make-up product in decorative cosmetics, for example, as dry powder formulations of minerals, natural minerals and earth-derived pigments. For administration, the botanical antioxidant blend of the invention can be topically applied to the skin in cosmetic and dermatological compositions of the invention in the manner conventional for cosmetics.

Cosmetic and dermatological compositions of the invention can exist in various forms. For example, the compositions of the invention can be in the form of a cream, a solution, a serum, an anhydrous preparation, an emulsion or microemulsion of the type water-in-oil (W/O) or of the type oil-in-water (O/W), a multiple emulsion, for example of the type water-in-oil-in-water (W/O/W), a gel, a solid stick, an ointment, an aerosol, or a dry powder. It is also advantageous to administer a botanical antioxidant blend of the invention in encapsulated form, for example in collagen matrices and other conventional encapsulation materials, for example as cellulose encapsulations, in gelatin, in wax matrices or as liposomal encapsulations. Preferably the composition of the invention is in the form of a cream. It is also possible and advantageous within the scope of the present invention to add a botanical antioxidant blend of the invention to aqueous systems or surfactant compositions for cleansing the skin.

Emulsions according to the present invention are advantageous and contain, for example, the afore-mentioned fats, oils, waxes and other adipoids, and water and an emulsifier, as is used conventionally for such a type of formulation.

The lipid phase can advantageously be selected from the following substance group: mineral oils, mineral waxes; oils, such as triglycerides of capric or caprylic acid, also natural oils, such as for example castor oil; fats, waxes and other natural and synthetic adipoids, preferably esters of fatty acids with alcohols of low carbon number (e.g., $C_{2-8}$), for example with isopropanol, propylene glycol or glycerine, or esters of fatty alcohols with alkane acids of low carbon number or with fatty acids; alkyl benzoates; silicone oils, such as dimethylpolysiloxanes, diethylpolysiloxanes, diphenylpolysiloxanes and mixtures thereof.

The oil phase of the emulsions, oleogels or hydrodispersions or lipodispersions within the scope of the present invention is advantageously selected from the group of esters of saturated and/or unsaturated, branched and/or unbranched alkane carboxylic acids of chain length from 3 to 30 carbon atoms and saturated and/or unsaturated, branched and/or unbranched alcohols of chain length from 3 to 30 carbon atoms, from the group of esters from aromatic carboxylic acids and saturated and/or unsaturated, branched and/or unbranched alcohols of chain length from 3 to 30 carbon atoms. Such ester oils can then advantageously be selected from the group isopropyl myristate, isopropyl palmitate, isopropyl stearate, isopropyl oleate, n-butyl stearate, n-hexyl laurate, ndecyloleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic, and natural mixtures of such esters, for example jojoba oil.

Furthermore, the oil phase can advantageously be selected from the group of branched and unbranched hydrocarbons and waxes, silicone oils, dialkyl ethers, the group of saturated or unsaturated, branched or unbranched alcohols, and fatty acid triglycerides, namely the triglycerine esters of saturated and/or unsaturated, branched and/or unbranched alkane carboxylic acids of chain length from 8 to 24, in particular 12-18, carbon atoms. The fatty acid triglycerides can advantageously be selected, for example from the group of synthetic, semi-synthetic and natural oils, for example olive oil, sunflower oil, soybean oil, peanut oil, rape-seed oil, almond oil, palm oil, coconut oil, palm kernel oil and the like.

Also any mixtures of such oil and wax components can be used advantageously within the scope of the present invention. It can also optionally be advantageous to use waxes, for example cetyl palmitate, as the single lipid component of the oil phase.

The oil phase is advantageously selected from the group 2-ethylhexyl isostearate, octyl-5-dodecanol, isotridecyl isononanoate, isoeicosane, 2-ethylhexyl cocoate, $C_{12-15}$ alkyl benzoate, capryl-capric acid triglyceride, dicaprylyl ether.

Mixtures of $C_{12-15}$ alkyl benzoate and 2-ethylhexyl isostearate, mixtures of $C_{12-15}$ alkyl benzoate and isotridecyl isononanoate and mixtures of $C_{12-15}$ alkyl benzoate, 2-ethylhexyl isostearate and isotridecyl isononanoate are particularly advantageous.

Of the hydrocarbons, paraffin oil, squalane and squalene can be used advantageously within the scope of the present invention.

The oil phase can advantageously also contain cyclic or linear silicone oils or can consist completely of such oils, but wherein it is preferable, apart from the silicone oil or the silicone oils, to use an additional amount of other oil phase components.

Cyclomethicone (octamethylcyclotetrasiloxane) is advantageously employed as silicone oil to be used according to the invention. However, other silicone oils should also advantageously be used within the scope of the present invention, for example hexamethylcyclotrisiloxane, polydimethylsiloxane, poly(methylphenylsiloxane). Mixtures of cyclomethicone and isotridecyl isononanoate, of cyclomethicone and 2-20 ethylhexyl isostearate, are also particularly advantageous.

The aqueous phase of the compositions of the invention can optionally contain advantageously alcohols, diols or polyols of low C number, and their ethers, preferably ethanol, isopropanol, propylene glycol, glycerine, ethylene glycol, ethylene glycol monoethyl or monobutyl ether, propylene glycol monomethyl, monoethyl or monobutyl ether, diethylene glycol monomethyl or monoethyl ether and analogous products, also alcohols of low C number, for example ethanol, isopropanol, 1,2-propane diol, glycerine and, in particular, one or more thickening agents, which can advantageously be selected from the group silicon dioxide, aluminum silicates, polysaccharides or their derivatives, for example hyaluronic acid, xanthan gum, hydroxypropylmethylcellulose, particularly advantageously from the group of polyacrylates, in each case individually or in combination.

Mixtures of the above-mentioned solvents are used in particular. For alcoholic solvents, water can be a further constituent.

Gels according to the present invention conventionally contain alcohols of low carbon number (e.g., $C_{2-8}$), for example ethanol, isopropanol, 1,2-propane diol, glycerine and water or an above-mentioned oil in the presence of a thickening agent, which for oily-alcoholic gels is preferably silicon dioxide or an aluminum silicate, for aqueous-alcoholic or alcoholic gels is preferably a polyacrylate.

The conventionally-known, highly volatile, liquefied propellants, for example hydrocarbons (propane, butane, isobutane), which can be used alone or mixed with one another, are suitable as propellants for compositions which can be sprayed from aerosol containers according to the present invention. Compressed air can also advantageously be used.

Cosmetic compositions of the invention which are a skin-cleansing agent or shampooing agent preferably contain at least one anionic, non-ionic or amphoteric surfactant substance, or also mixtures of such substances, a botanical antioxidant blend of the invention in aqueous medium and auxiliaries, as are used conventionally therefore. The surfactant substance or the mixtures of these substances can be present in the shampooing agent in a concentration between 1 wt % and 50 wt %.

These cosmetic or dermatological compositions can also be aerosols having the auxiliaries conventionally used therefor.

Aqueous cosmetic cleansing agents of the invention or low-water or anhydrous cleansing agent concentrates intended for aqueous cleansing can contain anionic, non-ionic and/or amphoteric surfactants, for example traditional soaps, for example fatty acid salts of sodium alkyl sulphates, alkyl ether sulphates, alkane and alkyl benzene sulphonates, sulphoacetates, sulphobetaines, sarcosinates, amidosulphobetaines, sulphosuccinates, sulphosuccinic acid semiesters, alkyl ether carboxylates, protein-fatty acid condensates, alkylbetaines and amidobetaines fatty acid alkanol amides polyglycol ether derivatives.

Compositions of the invention which are cosmetic cleansing compositions for the skin, can be present in liquid or solid form. In addition to a botanical antioxidant blend of the invention, they preferably contain at least one anionic, non-ionic or amphoteric surfactant substance or mixtures thereof, if required one or more electrolytes and auxiliaries, as are used conventionally therefor. The surfactant substance can be present in the cleansing compositions in a concentration between 0.001 and 99.999 wt %, based on the total weight of the compositions.

Compositions of the invention which are a shampooing agent, in addition to a effective amount of a botanical antioxidant blend of the invention, preferably contain an anionic, non-anionic or amphoteric surfactant substance or mixture thereof, optionally an electrolyte of the invention and auxiliaries, as are used conventionally therefor. The surfactant substance can be present in the shampooing agent in a concentration between 0.001 wt % and 99.999 wt %.

The compositions of the invention contain, apart from the afore-mentioned surfactants, water and optionally the additives which are conventional in cosmetics, for example perfume, thickener, dyestuffs, deodorants, antimicrobial materials, back-fatting agents, complexing and sequestering agents, pearlescent agents, plant extracts, vitamins and/or their derivatives, active ingredients and the like.

Pro-oxidative degradation products may be reduced, eliminated or prevented when using a botanical antioxidant blend of the invention. The use of a botanical antioxidant blend of the invention and its use for combating and/or prophylaxis of skin aging caused by oxidative stress and inflammatory reactions are within the scope of the present invention.

The use of a botanical antioxidant blend of the invention for the stabilization of cosmetic or dermatological compositions, which contain as additive either vitamin A and/or its derivatives (for example, all-E-retinoic acid, 9-Z-retionoic acid, 13-Z-retinoic acid, retinal, retinyl ester), vitamin B and/or its derivatives, vitamin C and/or its derivatives and vitamin E and/or its derivatives (for example, alpha-tocopherol acetate) individually or in combination, is thus likewise within the scope of the present invention. The stabilizing effect of the present invention relates to both smell and color and in particular to the active ingredient content of the composition.

The use of a botanical antioxidant blend of the invention for the protection of the skin from oxidative stress is also regarded as an advantageous embodiment of the present invention.

The present invention also includes a cosmetic process for protecting the skin and the hair from oxidative or photooxidative processes, which is characterized in that a cosmetic agent, which contains an effective concentration of a botanical antioxidant blend of the invention, is applied to the skin or hair in adequate quantity.

Likewise, the present invention also includes a process for protecting cosmetic or dermatological compositions from oxidation or photo-oxidation, wherein these compositions, for example compositions for treating and caring for the hair are, in particular hair lacquers, shampooing agents, also make-up products, such as for example nail varnishes, lipsticks, foundations, washing and showering compositions, creams for treating or caring for skin or other cosmetic compositions, the constituents of which can bring with them stability problems due to oxidation or photo-oxidation on storage, characterized in that the cosmetic compositions have an effective amount of a botanical antioxidant blend of the invention.

The following examples further illustrate the invention but, of course, should not be construed as in any way limiting its scope.

An example of a suitable botanical antioxidant extract blend of the present invention is provided below.

| Botanical Extract (INCI) | Amount (wt. %) | ORAC Value[§] |
|---|---|---|
| First antioxidant botanical extract comprising chlorogenic acid, pyrogallol, protocatechuuic acid, p-trans-coumaric acid | 80 | 12,787 µmole |
| Second antioxidant botanical extract comprising catechins, epigallocatechin gallate, apigallocatechin, epicatechin gallate, epicatechin, kaempferol, quercetin, myricetin, vitamins B, C, E, gallic acid, chlorogenic acid and caffeic acid | 15 | 11,518 µmole |
| Third antioxidant botanical extract comprising resveratrol, catechins, anthocyanins, oligomeric proanthoyanidins, tannins, tocopherols | 3 | 4,974 µmole |
| Fourth antioxidant botanical extract comprising anthocyanins, proanthocyanidins, homoorientin, orientin, taxifolin, vitamin E, vitamin B, resveratrol, isovitexin | 1 | 149 µmole |
| Fifth antioxidant botanical extract comprising curcumininoids | 0.5 | 10,409 µmole |
| Sixth antioxidant botanical extract comprising polyphenols, catechins, proanthocyanidins, and tannins | 0.5 | 1,639 µmole |
| Total weight | 100 | |
| Predicted ORAC value | | 12,168 µmole* |
| Actual ORAC value | | 13,400 µmole |

[§]The ORAC result is expressed as micromole Trolox equivalency (µmole TE). The acceptable precision is ≤15% relative standard deviation. The ORAC values were determined according to the methods reported in Ou, B., et al. *J. Agric. and Food Chem.* 49(10): 4619-4626 (2001); Huang, D., et al., J. Agric. and Food Chem. 50(7): 1815-21 (2002); Ou, B., et al., "Method for Assaying the Antioxidant Capacity of A Sample," U.S. Pat. No. 7,132,296 B2.
*The Predicted ORAC value is determined based on the weighted average of the ORAC values for the constituent parts.

This exemplary botanical antioxidant extract blend can be formulated in any of the compositions discussed herein, including the various compositions illustrated below.

Compositions containing a botanical antioxidant blend of the present invention should preferably be free of sensitizing-agents (e.g., paraben). Suitable compositions according to the present invention can be prepared with various ingredients, as described below.

Facial Cleanser of the present invention containing: Aqua, Sodium Lauroyl Oat Amino Acids, Sodium $C_{12-16}$ Olefin Sulfonate, Cocamidopropylamine Oxide, Sodium Lactate, PEG-6 Caprylic/Capric Glycerides, Sucrose Polysoyate, PEG-6 Lauramide, Lactic Acid, CI 77891, Glycerin, Glycol Palmitate, Cetearyl Alcohol, Ceteareth-33, Salicylic Acid, Caprylic/Capric Triglyceride, Coco-Glucoside, Coconut Alcohol, *Cucumis Sativus* Fruit Extract, PEG-120 Methyl Glucose Dioleate, Hydroxyethylcellulose, Aluminum Hydroxide, Stearic Acid, Xanthan Gum, Citric Acid, Disodium EDTA, Phenoxyethanol and a botanical antioxidant extract blend of the invention.

Eye Serum of the present invention containing: Aqua, Sodium Lactate, Isopropyl Lauroyl Sarcosinate, PPG-3 Benzyl Ether Myristate, Algae Extract, CI 77891, Glycerin, Palmitoyl Tripeptide-3, Glycerine, Lactic Acid, Decenel-Butene Copolymer, Caffeine, Retinol, *Chondrus Crispus*, Phenyl Trimethicone, Cyclopentasiloxane, Phospholipids, Dimethiconol, Xanthan Gum, Glucose, Aluminum Hydroxide, Hydrated Silica, Alginic Acid, CI 77489, Silica, Sodium Polyacrylate, PVMIMA Copolymer, Cetearyl Olivate, Sorbitan Olivate, C20-22 Alkyl Phosphate, C20-22 Alcohols, Polysorbate 20, Acrylamide I Sodium Acryloyldimethyl Taurate Copolymer, Isohexadecane, Polysorbate 80, Hydroxyethylcellulose, Triethanolamine, Disodium EDTA, Phenoxyethanol, and a botanical antioxidant extract blend of the invention.

Moisturizing Facial Cream of the present invention containing: Aqua, Sodium Lactate, 10 CapryliclCapric Triglyceride, Bis-Hydroxyethoxypropyl Dimethicone, Glycerin, Isopropyl Lauroyl Sarcosinate, Lactic Acid, Cetearyl Glucoside, *Glycine Soja* Protein, Oxido Reductases, Retinol, Sodium Hyaluronate, Sodium PCA, Urea, Trehalose, *Chondrus Crispus*, Glucose, Isohexadecane, Polyquaternium-5 1, Sodium Polyacrylate, PVMIMA Copolymer, Xanthan Gum, Cetearyl Olivate, Sorbitan Olivate, Glyceryl Stearate, PEG-100 Stearate, Polysorbate 20, Acrylamide 1 Sodium Acryloyldimethyl Taurate Copolymer, Polysorbate 80, Hydroxyethylcellulose, Magnesium Aluminum Silicate, Steareth-100, CI 77891, Hydrogenated Glyceridic Oil, Disodium EDTA, Phenoxyethanol and a botanical antioxidant blend.

Treatment Peel of the present invention containing: Lactic Acid, Aqua, SD Alcohol 40-B, Ammonium Lactate, Salicylic Acid, botanical antioxidant extract blend of the invention and Hydroxyethylcellulose.

Alternative composition (e.g., cream) of the present invention containing: Aqua, Glycerin, Cetyl Ricinoleate, Isohexadecane, Ceresin, Glyceryl Stearate, Isopropyl Lauroyl Sarcosinate, Sericin, Dimethicone, PEG-60 Hydrogenated Castor Oil, Steareth-2, Sodium PCA, PEG-100 Stearate, CI 77891, Cholesterol, Ceramide 111, Linoleic Acid, Linolenic Acid, Tocopherol, *Panicum Miliaceum* Extract, Glycosaminoglycans, BHT, Propylene Glycol, Styrene Acrylates Copolymer, Hydrolyzed Corn Starch, Ammonium Hydroxide, PEG-30 Dipolyhydroxystearate, Cetyl Hydroxyethylcellulose, Xanthan Gum, Magnesium Aluminum Silicate, Disodium EDTA, Phenoxyethanol and a botanical antioxidant extract blend of the invention.

Alternative composition (e.g., cream) of the present invention containing: Aqua, Sodium Lactate, Glycerin, Sucrose Cocoate, Lactic Acid, Isohexadecane, Isopropyl Lauroyl Sarcosinate, Glyceryl Stearate, PEG-100 Stearate, Sorbitan Stearate, Steareth-2, CI 77891, Magnesium Aluminum Silicate, PEG-60 Hydrogenated Castor Oil, Butylene Glycol, Methyl Dihydroxybenzoate, Retinol, Tocopherol, Magnesium Ascorbyl Phosphate, BHT, Bisabolol, Allantoin Glycyrrhetinic Acid, Dimethicone, Polysorbate 20, PEG-30 15 Dipolyhydroxystearate, Xanthan Gum, Cetyl Hydroxyethylcellulose, Disodium EDTA, Propylene Glycol, Styrene Acrylates Copolymer, Hydrolyzed Corn Starch, Ammonium Hydroxide, Phenoxyethanol and a botanical antioxidant extract blend of the invention.

Sun Protector of the present invention containing: Zinc Oxide, Octinoxate, Oxybenzone, Octisalate, Aqua, Dicaprylyl Carbonate, PEG-20 Stearate, Pentylene Glycol, Glyceryl Stearate, Laureth-23, Silica, Bis-Hydroxyethoxypropyl Dimethicone, Cetearyl Alcohol, Coco-Glucoside, *Butyrospermum Parkii* Extract, Phospholipids, Cyclopentasiloxane, Cyclohexasiloxane, Butylene Glycol, Caprylic/Capric Triglyceride, Ascorbyl Tetraisopalmitate, Tocopherol, Carbomer, Sodium DNA, Cetyl Hydroxyethylcellulose, Potassium Cetyl Phosphate, Hydrogenated Palm Glycerides, Dimethoxydiphenylsilane/Triethoxycaprylylsilane Crosspolymer, Xanthan Gum, Disodium EDTA, Diazolidinyl Urea, Iodopropynyl Butylcarbamate and a botanical antioxidant extract blend of the invention.

Environmental Protector of the present invention containing: Aqua, Glycerin, Dipropylene Glycol, Glyceryl Stearate, PEG-100 Stearate, Stearyl Alcohol, Ceteareth-20, Cetyl Hydroxyethylcellulose, Xanthan Gum, Disodium EDTA, Phenoxyethanol and a botanical antioxidant extract blend of the invention.

Dry mineral powder of the invention containing: Zinc Oxide, Titanium Dioxide, Bismuth Oxychloride, Mica, Iron Oxide, and a botanical antioxidant extract blend of the invention.

Prophetic Composition (e.g., body cream) of the present invention containing at least: botanical antioxidant extract blend of the invention, Xanthin (e.g., Caffeine), AHA (Lactic Acid), and Stimulators of Collagen Synthesis (as, e.g., Vitamin C and derivatives thereof).

All references, including publications, patent applications, and patents, cited herein are hereby incorporated by reference to the same extent as if each reference were individually indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of improving the appearance of skin, comprising topically administering to a subject in need thereof a botanical antioxidant composition comprising
   a botanical antioxidant extract blend comprising:
   (a) a hydroxycinnamic acid in an amount of at least 50 wt. %, based on a total blend weight; and
   (b) a *camellia sinesis* extract, a *vitis vinifera* extract, a *euterpe oleracea* extract, a *curcuma longa* extract, and/or a *theobroma cacao* extract,
   wherein the composition is in cream, lotion, solution, serum, anhydrous preparation, emulsion, microemulsion, multiple emulsion, gel, solid stick, ointment, dry powder, spray, or aerosol form.

2. The method of claim 1, wherein the blend has an oxygen radical absorbance capacity (ORAC) value greater than the weight averaged individual ORAC values of blend components.

3. The method of claim 1, wherein the improving the appearance of skin comprises reducing at least one of skin wrinkling, fine lines, skin sagging, skin dryness, skin thinness, skin transparency, skin firmness, aged skin smoothness, skin blotchiness, skin darkening, age spots, spider veins, actinic keratoses, nail plate thinning, nail plate ridging, cellulitis, rosacea, acne, eczema, dermatitis, or pruritis.

4. The method of claim 1, wherein the improving the appearance of skin comprises preventing at least one of damage to lipids, preventing damage to DNA, preventing damage to proteins, protecting the skin against photo-reactions, and/or protecting the skin against inflammatory reactions.

5. The method of claim 1, comprising two or more of the *camellia sinesis, vitis vinifera, euterpe oleracea, curcuma longa*, and/or *theobroma cacao* extract.

6. The method of claim 1, comprising three or more of the *camellia sinesis, vitis vinifera, euterpe oleracea, curcuma longa*, and/or *theobroma cacao* extract.

7. The method of claim 1, comprising four or more of the *camellia sinesis, vitis vinifera, euterpe oleracea, curcuma longa*, and/or *theobroma cacao* extract.

8. The method of claim 1, comprising the *camellia sinesis* extract, *vitis vinifera* extract, *euterpe oleracea* extract, *curcuma longa* extract, and *theobroma cacao* extract.

9. The method of claim 1, wherein the blend comprises 70 wt. % or more of the hydroxycinnamic acid, based on the total blend weight.

10. The method of claim 1, wherein the blend comprises about 80 wt. % or more of the hydroxycinnamic acid, based on the total blend weight.

11. The method of claim 1, wherein the hydroxycinnamic acid comprises alpha-cyano-4-hydroxycinnamic acid, caffeic acid, cichoric acid, cinnamic acid, chlorogenic acid, caftaric acid, coumarin, coumaric acid, coutaric acid, diferulic acid, fertaric acid, ferulic acid, sinapinic acid, or a mixture of two or more thereof.

12. The method of claim 1, wherein the hydroxycinnamic acid comprises chlorogenic acid.

13. The method of claim 1, comprising 0.001 to 20 wt. % of the blend, based on a total composition weight.

14. The method of claim 1, wherein the composition further comprises a surfactant, cosmetic auxiliary, pigment, UVA filter, UVB filter, propellant, thickening agent, emulsifier, solvent, water, antioxidant, perfume, dyestuff, deodorant, antimicrobial material, back-fatting agent, complexing agent, sequestering agent, pearlescent agent, exfoliating agent, further plant extract, vitamin, or mixture of two or more of these.

15. A method of stabilizing formulation ingredients in a cosmetic or dermatological composition, the method comprising combining components of a botanical antioxidant blend comprising:
   (a) a hydroxycinnamic acid in an amount of at least 50 wt. %, based on a total blend weight; and
   (b) a *camellia sinesis* extract, *vitis vinifera* extract, *euterpe oleracea* extract, *curcuma longa* extract, and/or *theobroma cacao* extract,
   wherein the composition is in cream, lotion, solution, serum, anhydrous preparation, emulsion, microemulsion, multiple emulsion, gel, solid stick, ointment, dry powder, of aerosol form.

16. The method of claim 15, wherein the blend has an oxygen radical absorbance capacity (ORAC) value greater than the weight averaged individual ORAC values of blend components.

17. The method of claim 15, comprising two or more of the *camellia sinesis, vitis vinifera, euterpe oleracea, curcuma longa*, and/or *theobroma cacao* extract.

18. The method of claim 15, comprising three or more of the *camellia sinesis, vitis vinifera, euterpe oleracea, curcuma longa*, and/or *theobroma cacao* extract.

19. The method of claim 15, comprising four or more of the *camellia sinesis, vitis vinifera, euterpe oleracea, curcuma longa*, and/or *theobroma cacao* extract.

20. The method of claim 15, wherein the blend comprises 70 wt. % or more of the hydroxycinnamic acid, based on the total blend weight.

21. The method of claim 15, wherein the hydroxycinnamic acid comprises chlorogenic acid.

22. A method of improving the appearance of skin, comprising topically administering to a subject in need thereof a botanical antioxidant composition comprising
   0.001 to 20 wt. % a botanical antioxidant extract blend, based on a total composition weight, comprising:
   (a) a hydroxycinnamic acid in an amount of at least 50 wt. %, based on a total blend weight; and
   (b) a *camellia sinesis* extract, a *euterpe oleracea* extract, a *curcuma longa* extract, and/or a *theobroma cacao* extract,
   wherein the composition is in cream, lotion, solution, serum, anhydrous preparation, emulsion, microemulsion, multiple emulsion, gel, solid stick, ointment, dry powder, spray, or aerosol form.

23. The method of claim 22, comprising two or more of a *vitis vinifera* extract, the *camellia sinesis, euterpe oleracea, curcuma longa*, and/or *theobroma cacao* extract.

24. The method of claim 22, comprising three or more of a *vitis vinifera* extract, the *camellia sinesis, euterpe oleracea, curcuma longa*, and/or *theobroma cacao* extract.

* * * * *